United States Patent
Wall

(10) Patent No.: US 7,092,850 B2
(45) Date of Patent: *Aug. 15, 2006

(54) SENSOR SIGNAL DEBOUNCING

(75) Inventor: Gary C. Wall, Allen, TX (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/238,442

(22) Filed: Sep. 29, 2005

(65) Prior Publication Data

US 2006/0025960 A1 Feb. 2, 2006

Related U.S. Application Data

(63) Continuation-in-part of application No. 10/779,969, filed on Feb. 17, 2004, now Pat. No. 6,957,174.

(51) Int. Cl.
*G06F 15/00* (2006.01)
(52) U.S. Cl. ..................................... 702/189
(58) Field of Classification Search ............... 702/189; 374/1, 171–172
See application file for complete search history.

(56) References Cited

U.S. PATENT DOCUMENTS 6,788,202 B1 9/2004 Holmes et al.
6,806,729 B1 * 10/2004 Wallace et al. ............... 326/33
6,816,023 B1 11/2004 Currier et al.
6,957,174 B1 * 10/2005 Wall ........................... 702/189
2002/0190858 A1 * 12/2002 Holmes et al. ............. 340/541
2005/0182579 A1 8/2005 Wall

* cited by examiner

*Primary Examiner*—John Barlow
*Assistant Examiner*—Cindy D. Khuu

(57) ABSTRACT

One disclosed method includes retrieving a sensor reading, incrementing a reading change counter and setting a stable reading counter in response to the sensor reading not equaling an immediately previous sensor reading, reporting a sensor reading bouncing error and resetting the reading change counter in response to the reading change counter being greater than or equal to a reading change tolerance, incrementing the stable reading counter in response to the sensor reading equaling the immediately previous sensor reading, resetting the stable reading counter and reading change counter in response to the stable reading counter being greater than or equal to a stable reading tolerance, reporting a state change event and setting the most-recent stable sensor reading equal to the sensor reading in response to the sensor reading not being equal to the most-recent stable sensor reading, and setting the previous sensor reading to the sensor reading.

21 Claims, 2 Drawing Sheets

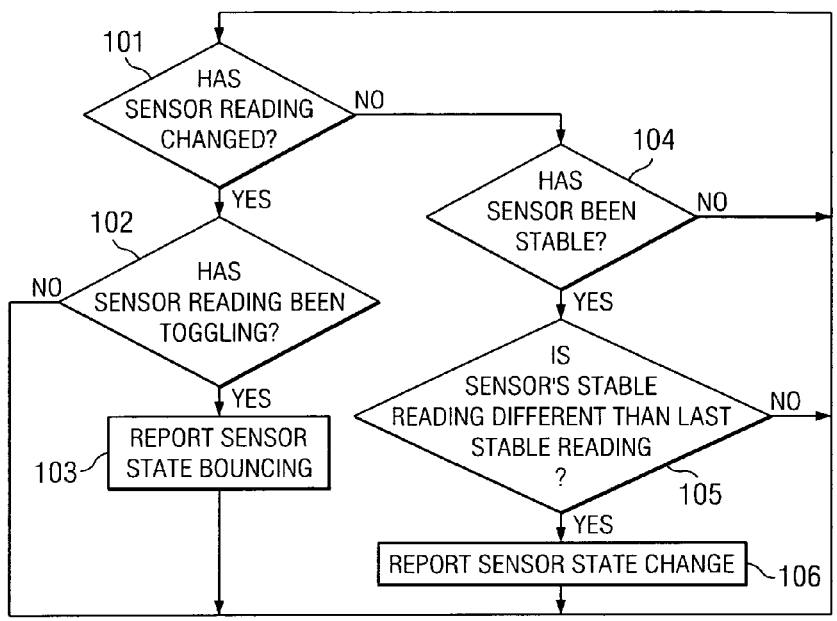
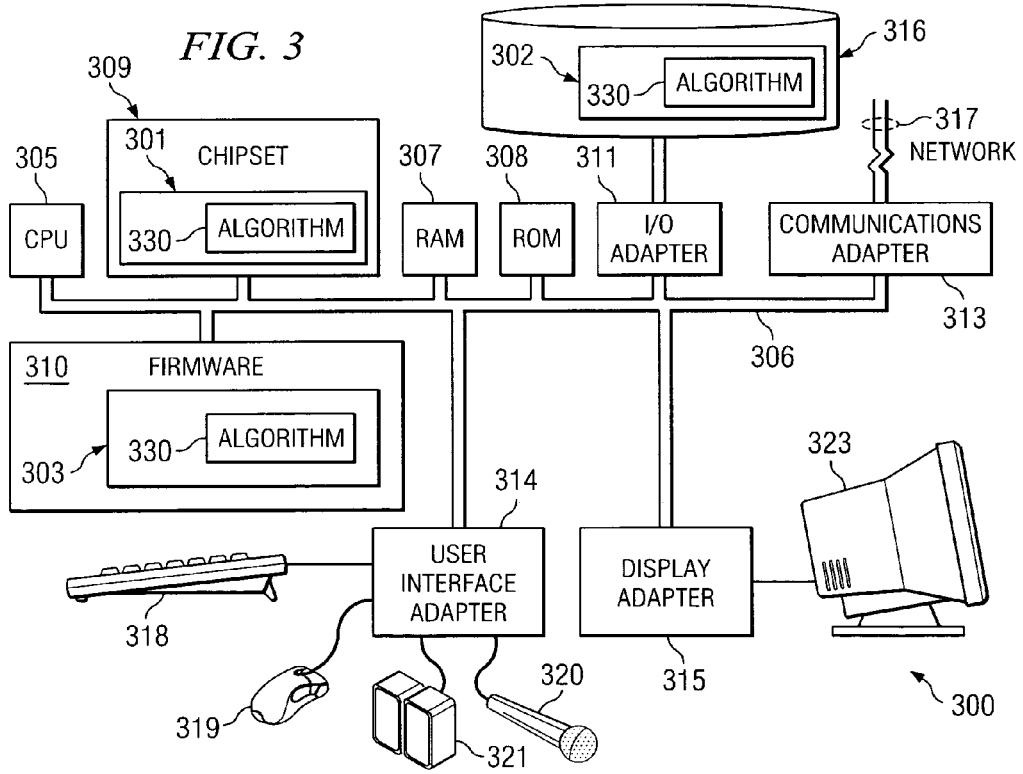

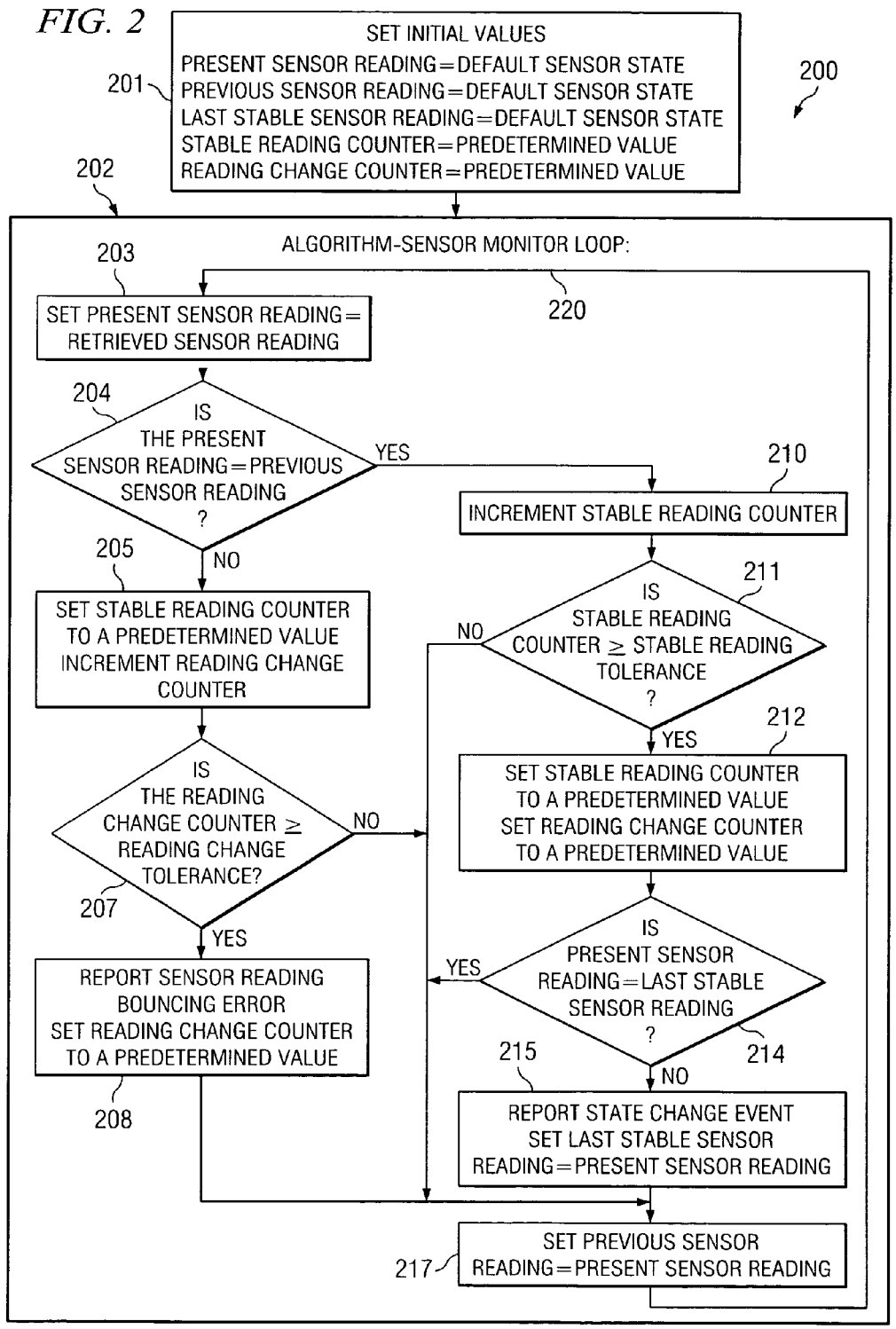

SENSOR SIGNAL DEBOUNCING

CROSS-REFERENCE TO RELATED APPLICATIONS

The present application is a continuation-in-part of U.S. patent application Ser. No. 10/779,969, entitled "SENSOR SIGNAL DEBOUNCING", filed Feb. 17, 2004 now U.S. Pat. No. 6,957,174, the disclosure of which is incorporated herein by reference.

BACKGROUND

Sensor signals can often have characteristics such that under some set of conditions the sensor signals give erroneous readings. For example, sensor signals indicating the presence of a device may, during the addition or deletion of a device to a system while the system is active, toggle between present and not present. Errant sensor signals may also be generated during a ramp-up of power for an added device. Errant sensor signals may also be generated due to malfunctions in an Integrated Circuit (IC). In these and other situations multiple sensor state changes may be falsely sensed and reported.

Following a de facto process of waiting a certain time before looking at a sensor signal, thereby allowing the sensor signal time to debounce, two approaches are customarily taken to handle sensor signals that are sensitive to other events. In the first of these approaches some error reports related to the sensor signal are accepted as issues with the product and ignored by the event consumer. Herein, the "event consumer" may be an application program, an operating system, a firmware entity, hardware entity, or the like. In certain circumstances it may be a user of the associated processor-based system. In the aforementioned first existing approach taken to handle sensor signals that are sensitive to other events, an initial value of a present sensor reading and a previous sensor reading are each set as equal to a default sensor state value. Then an algorithm, which may be referred to as a sensor monitor loop, is executed, wherein the present sensor reading is set equal to a retrieved sensor reading. If the present sensor reading is not equal to the previous sensor reading, a state change event is reported and the previous sensor reading is set as equal to the present sensor reading. The sensor monitor loop is then repeated.

Problematically, in this first approach it is difficult to distinguish erroneous reports from actual events. Also, under this first approach sensor-signal glitches often force the reporting of multiple events in quick succession, many of which are erroneous.

In a second existing approach, often referred to as signal debouncing, a sensor signal is read multiple times to determine if it is stable, prior to reporting a state change. In this second existing approach, initial values for a present sensor reading, a previous sensor reading and a last stable sensor reading are each set as equal to a default sensor state value. An initial value of a stable reading counter is initially set at zero. An algorithm, which may also be labeled a sensor monitor loop, sets the present sensor reading as equal to a retrieved sensor reading. If the present sensor reading is equal to the previous sensor reading, a stable reading counter is incremented. If the present sensor reading is not equal to the previous sensor reading, a stable reading counter is zeroed. However, if the stable reading counter is greater than or equal to a stable reading tolerance level, the stable reading counter is zeroed. If in addition to the stable reading counter being greater than or equal to a stable reading tolerance level, the present sensor reading is not equal to the last stable sensor reading, a state change event is reported. The last stable sensor reading and previous sensor reading are then set to be the present sensor reading. The sensor monitor loop is then repeated.

Problematically, this second approach may mask out actual errors where the sensor signal is metastable. Herein, "metastable" refers to a condition wherein a sensor signal continues to transition above and below a threshold that would indicate one signal state or another. Typically, a metastable sensor signal never holds at a state long enough to be considered at that value. Problematically, a metastable sensor signal may transition at some frequency greater than the number of samples required to determine that the transient state should be reported. Thus, the latter approach for signal debouncing might filter out true instability, such as where the frequency of a metastability is higher than the required threshold hold time to report a state change, thereby possibly never reporting a state change.

SUMMARY

An embodiment of A method comprises retrieving a present sensor reading, incrementing a reading change counter and setting a stable reading counter to a predetermined value in response to the present sensor reading not equaling an immediately previous sensor reading, reporting a sensor reading bouncing error and resetting the reading change counter to a predetermined value in response to the reading change counter being greater than or equal to a reading change tolerance, incrementing the stable reading counter in response to the present sensor reading equaling the immediately previous sensor reading, resetting the stable reading counter and reading change counter to a predetermined value in response to the stable reading counter being greater than or equal to a stable reading tolerance, reporting a state change event and setting the most-recent stable sensor reading equal to the present sensor reading in response to the present sensor reading not being equal to the most-recent stable sensor reading, and setting the previous sensor reading to the present sensor reading.

Another embodiment of a method comprises retrieving a present sensor reading, determining if the present sensor reading equals an immediately previous sensor reading, incrementing a reading change counter and setting a stable reading counter to a predetermined value in response to the present sensor reading not equaling an immediately previous sensor reading, determining if a change in the reading change counter is greater than or equal to a reading change tolerance, reporting a sensor reading bouncing error and resetting the reading change counter to a predetermined value in response to the reading change counter being greater than or equal to a reading change tolerance, incrementing said stable reading counter in response to the present sensor reading equaling the immediately previous sensor reading, determining if a change in said stable reading counter is greater than or equal to a stable reading tolerance, resetting said stable reading counter and reading change counter to a predetermined value in response to said stable reading counter being greater than or equal to a stable reading tolerance, determining if said present sensor reading is not equal to said most-recent stable sensor reading, reporting a state change event and setting said most-recent stable sensor reading equal to said present sensor reading in response to said present sensor reading not being equal to said most-recent stable sensor reading, and setting said previous sensor reading to said present sensor reading.

An embodiment of a computer program product comprises a computer usable medium having computer readable program code means embodied therein for causing a computer to, in iterative fashion: retrieve a sensor reading, determine if said sensor reading represents a changed sensor reading, increment a reading change counter and set a stable reading counter to a predetermined value in response to the sensor reading having changed, determine if a changed sensor reading is indicative of toggling, report a sensor reading bouncing error and reset the reading change counter to a predetermined value in response to the reading change indicating the sensor reading is toggling, increment said stable reading counter in response to the sensor reading having not changed, determine if the unchanged sensor reading is stable, reset said stable reading counter and said reading change counter to a predetermined value in response then unchanged sensor reading being stable, determine if a stable unchanged sensor reading is different from a most-recent stable sensor reading, report a state change event and set said most-recent stable sensor reading to be equal to the stable unchanged sensor reading, and set a previous sensor reading to be equal to said sensor reading.

BRIEF DESCRIPTION OF THE DRAWINGS

FIG. 1 is a flow chart of an embodiment of the present methods;

FIG. 2 is a more detailed flow chart of an embodiment of the present methods; and FIG. 3 is a diagrammatic illustration of an embodiment of a general purpose processor-based system adapted to employ embodiments of the present systems.

DETAILED DESCRIPTION

In accordance with embodiments of the present systems and methods, sensor signal debouncing is employed to reduce false state reporting and to avoid alerting the event consumer to known device characteristics. The present systems and methods also address actual errors occurring where a sensor signal remains metastable, preferably detecting and reporting such occurrences. Preferably, the present systems and methods reduce the number of events that are reported so the event consumer is not overwhelmed with sensor signal reports. The present systems and methods also preferably sense and report when a sensor signal is bouncing. The present systems and methods may employ an algorithm for sensor signal handling, as detailed below, that detects metastable sensor signals while reducing the number of event reports to the event consumer. At the same time the signal is preferably debounced so only states that are maintained for a sufficient period of time are reported. The present systems and methods take into account that multiple transitions may occur within a hold time and recognizes these transitions as stability, through use of a counter or the like. Once a predetermined threshold or tolerance is reached a metastable signal is preferably reported to the event consumer, typically as a problem.

FIG. 1 is a flow chart of embodiment 100 of the present methods for sensor signal debouncing and metastable signal detection. At 101 a sensor signal may be read and a determination made as to whether the sensor reading indicates that the sensor signal reading has changed since a last sensor signal reading. If the sensor reading has changed a determination may be made at 102 as to whether the reading is toggling. The determination as to whether the reading is toggling may be made by determining if a count of changes in the sensor state value has achieved a predetermined threshold. If it is determined at 102 that the sensor reading is toggling a bouncing sensor-state error may be reported at 103. If it is determined at 101 that the sensor reading has not changed a determination may be made at 104 as to whether the sensor reading is stable. The determination as to whether the sensor reading is stable may be made by determining if a count of stable sensor readings is greater than or equal to a predetermined stable reading sensor tolerance. If the sensor reading is stable, a determination may be made at 105 as to whether the sensor reading is different from a most-recent stable sensor reading. If the sensor reading is different that a most-recent stable sensor reading a sensor state change may be reported at 106. However, if at 102 it is determined that the sensor reading is not toggling, at 104 that the sensor reading is not stable, or at 105 that the sensor reading is the same as a most-recent stable sensor reading, then process 100 is restarted with a new sensor reading. Process 100 may be employed to monitor the changes in a sensor state value for a predetermined period of time or indefinitely.

FIG. 2 is a flow chart of embodiment 200 of the present methods for sensor signal debouncing and metastable signal detection. At 201 initial values for a present sensor reading, a previous sensor reading, and a most-recent stable sensor reading are set as equal to a default sensor state value. Also at 201, a stable reading counter and reading change counter are set to a predetermined value, such as zero. An algorithm may employ a loop, such as may be labeled as a sensor monitor loop (202). A sensor state value is read and sensor monitor loop 202 sets the present sensor reading as equal to the retrieved sensor reading at 203. Then a determination is made as to whether the sensor state value has changed at 204. If it is determined at 204 that the present sensor reading does not equal the previous sensor reading, the stable reading counter is set or reset to a predetermined value, such as zero, and the reading change counter is incremented at 205. A determination is made at 207 as to whether a count of changes in the sensor state value has achieved a threshold tolerance. If it is determined at 207 that the reading change counter is greater than or equal to a predetermined reading change tolerance value, a sensor reading bouncing event error is reported and the reading change counter is set to a predetermined value, such as zero, at 208. The reading change counter is reset at 208 so that future or continuing sensor reading bouncing events may be reported. Conversely, if it is determined at 207 that the reading change counter is less than the reading change tolerance value the previous sensor reading is then set as equal to the present sensor reading at 217 and sensor monitor loop 202 is repeated (220). The reading change tolerance employed at 207 is preferably a threshold that has been set to provide optimal debouncing in accordance with the present systems and methods.

However, if it is determined at 204 that the present sensor reading is equal to the previous sensor reading, the stable reading counter is incremented at 210. Then if the stable reading counter is determined to be greater than or equal to the stable reading tolerance value at 211, the stable reading counter and the reading change counter are set to a predetermined value, such as zero, at 212. Then if it is determined at 214 that the present sensor reading is not equal to the most-recent stable sensor reading, indicating the sensor state value has reached a new stable value, a true state change event is reported and the most-recent stable sensor reading is set to be equal to the present sensor reading at 215. The previous sensor reading is then set as equal to the present sensor reading and sensor monitor loop 202 is repeated (220). Similarly, if it is determined at 211 that the stable reading counter is less than the stable reading tolerance value, or at 214 that the present sensor reading is equal to the most-recent stable sensor reading the previous sensor reading is then set as equal to the present sensor reading at 217 and sensor monitor loop 202 is repeated (220). Changes in sensor state values may be monitored for a predetermined period of time, or indefinitely, through the use of sensor monitor loop 202 such that the tolerances at 207 and 211 may be tested.

It should be appreciated that reference is made above to setting or resetting a stable reading counter or reading change counter to a predetermined or default value. As indicated above, this default value may be zero. However, this value may be any value, which may be predetermined as indicated, or may in alternative embodiments, be randomly generated. Regardless, in accordance with embodiments of the present systems and methods, the initial predetermined or default value is maintained and is employed to make determinations in accordance therewith. For example, only a determination of the whether an increase in the reading change counter is greater than the reading change tolerance is needed at 207. Similarly, at 211 only a determination of whether an increase in the stable reading counter is greater than the stable reading tolerance need be made.

FIG. 3 is a diagrammatic illustration of an embodiment of general purpose processor-based system 300 adapted to employ embodiments 301, 302 and/or 303 of the present systems and methods. The present systems and methods may be practiced at different levels within processor-based system 300. The present systems and methods may be implemented in hardware (301) such as ROM 308 or chipset 309 of system 300. The present systems and methods may be implemented as software 302 that is monitoring hardware of system 300. Alternatively or additionally, systems and methods of the present invention may be implemented through embodiment 303 in firmware 310, or the like. When implemented via computer-executable instructions, various elements of embodiments 301, 302 or 303 of the present invention are in essence code, defining operations of such various elements.

One, two or all three of embodiments 301, 302 and 303 may be in operation on system 300 at one time. However, hardware embodiment 301 may be particularly well suited to be employed during boot and operation of system 300 to monitor for sensor signals. Embodiment 302 may be embodied in a software application that may be stored in mass storage 316, and may be particularly well suited to be called by processes or applications run by CPU 305. Whereas firmware 310 may be associated with particular Input-Output (I/O) functions of system 300 and firmware embodiment 303 may be particularly well suited to monitor signals for such I/O functions. Hardware embodiment 301, application 302 and/or firmware embodiment 303 may run as a background processes, in a manner known to those of ordinary skill in the art, monitoring for sensor signals.

FIG. 3 illustrates example computer system 300 adapted according to embodiments 301, 302 and 303 of the present invention. That is, computer system 300 comprises an example system on which embodiments 301, 302 and 303 of the present invention may be implemented. Central processing unit (CPU) 305 is coupled to system bus 306. CPU 305 may be any general purpose CPU. Suitable processors include without limitation any processor from HEWLETT-PACKARD's, HEWLETT-PACKARD's PA-8500 family of processors, or INTEL's PENTIUM® or ITANIUM families of processors, as examples. However, the present invention is not restricted by the architecture of CPU 305 as long as CPU 305 supports the inventive operations as described herein. CPU 305 may execute the various logical instructions according to embodiments of the present invention. For example, CPU 305 may execute machine-level instructions according to the exemplary operational flows described above in conjunction with FIGS. 1 and/or 2. Chipset 309 might comprise microchips needed to serve as a communications controller between CPU 305, memory 307 and 308, and other devices in computer system 300.

Computer system 300 also preferably includes random access memory (RAM) 307, which may be SRAM, DRAM, SDRAM, or the like. Computer system 300 preferably includes read-only memory (ROM) 308 which may be PROM, EPROM, EEPROM, or the like. Hardware embodiment 301 of the present invention may be embodied in ROM 308 and/or a chipset 309. Computer system 300 may also include firmware 310 that may control various aspects of operation of system 300. Ram 307, ROM 308, and firmware 310 may hold user and system data and programs, as is well known in the art.

Computer system 300 also preferably includes I/O adapter 311, communications adapter 313, user interface adapter 314, and display adapter 315. I/O adapter 311, user interface adapter 314, and/or communications adapter 313 may, in certain embodiments, enable a user to interact with computer system 300 in order to input information.

I/O adapter 311 preferably connects to storage device(s) 316, such as one or more of hard drive, compact disc (CD) drive, floppy disk drive, tape drive, etc. to computer system 300. Communications adapter 313 is preferably adapted to couple computer system 300 to network 317 (e.g., a Local Area Network, a Wide Area Network, an Intranet, the Internet, or the like). User interface adapter 314 couples user input devices, such as keyboard 318, pointing device 319, and microphone 320 and/or output devices, such as speaker (s) 321 to computer system 300. Display adapter 315 is driven by CPU 305 to control the display on display device 323 to, for example, to display user reports of state change events or errors described above.

Sensor signals may be provided when a peripheral or user input device, such as a digital camera, printer, keyboard 318, pointing device 319, microphone 320, speakers 321, and/or the like are connected or disconnected from computer system 300. For example, sensor signals may indicate the presence or absence of a device during the addition or deletion of the device to an active computer. However, errant sensor signals may be generated during a ramp-up of power for such an added device. Errant sensor signals may also be generated due to malfunctions in an IC associated with the system or a connected device such as the aforementioned peripheral or user input devices.

Each of embodiments, 301, 302 and 303, of the present invention preferably employs algorithm 330 to keep track of the number of sensor signal transitions that occur over time, report error states, and if a stable case is encounter, to report a transition event and restart the count of sensor signal transitions. As discussed in greater detail above in relation to FIGS. 1 and 2 algorithm 330 may read a sensor state, determine from this reading is the sensor state has changed. Then if the sensor state has changed, algorithm 330 may monitor that change for a certain period of time to determine if the number of changes indicate that a false event should be reported back to the event consumer. As pointed out above the event consumer may not necessarily be a user of system 300, but may be an application program running on system 300 or the operating system for system 300. During the time that algorithm 330 monitors the sensor state it may also read the sensor state's stability to see if the sensor state is reaching a stable value that warrants reporting back to the event consumer as a state change.

Pseudo code describing algorithm 330 appears below:

```
Initial values:
    presentSensorReading = defaultSensorState
    previousSensorReading = defaultSensorState
    lastStableSensorReading = defaultSensorState
    stableReadingCounter = default value
    readingChangeCounter = default value
Algorithm:
    Label SensorMonitorLoop:
        presentSensorReading = getSensorReading( )
        if (presentSensorReading != previousSensorReading)
            stableReadingCounter = default value
            readingChangeCounter ++
            if (readingChangeCounter >= ReadingChangeTolerance)
                ReportEvent(SensorReadingBouncing)
                readingChangeCounter = default value
        else
            stableReadingCounter++
            if (stableReadingCounter >= StableReadingTolerance)
                stableReadingCounter = default value
                readingChangeCounter = default value
                if(presentSensorReading != lastStableSensorReading)
                    ReportEvent(StateChange)
                lastStableSensorReading = presentSensorReading
        previousSensorReading = presentSensorReading
Goto SensorMonitorLoop
```

It shall be appreciated that the present invention is not limited to the architecture of system 300. For example, any suitable processor-based device or collection of devices may utilize the present invention, including without limitation personal computers, laptop computers, computer workstations, and multi-processor or multi-nodal servers. Moreover, embodiments of the present invention may be implemented on application specific integrated circuits (ASICs) or very large scale integrated (VLSI) circuits. Persons of ordinary skill in the art may utilize any number of suitable structures capable of executing logical operations according to the embodiments of the present invention.

What is claimed is:

1. A method comprising:
    retrieving a present sensor reading;
    incrementing a reading change counter and setting a stable reading counter to a predetermined value in response to the present sensor reading not equaling an immediately previous sensor reading;
    reporting a sensor reading bouncing error and resetting the reading change counter to a predetermined value in response to the reading change counter being greater than or equal to a reading change tolerance;
    incrementing said stable reading counter in response to the present sensor reading equaling the immediately previous sensor reading;
    resetting said stable reading counter and reading change counter to a predetermined value in response to said stable reading counter being greater than or equal to a stable reading tolerance;
    reporting a state change event and setting said most-recent stable sensor reading equal to said present sensor reading in response to said present sensor reading not being equal to said most-recent stable sensor reading; and
    setting said previous sensor reading to said present sensor reading.

2. The method of claim 1 further comprising repeating said retrieving, incrementings, reportings, resetting and setting.

3. The method of claim 1 further comprising repeating said retrieving, incrementings, reportings, resetting and setting in response to the reading change counter being less than a reading change tolerance.

4. The method of claim 1 further comprising repeating said retrieving, incrementings, reportings, resetting and setting in response to said stable reading counter being less than a stable reading tolerance.

5. The method of claim 1 further comprising repeating said retrieving, incrementings, reportings, resetting and setting in response to said present sensor reading being equal to said most-recent stable sensor reading.

6. The method of claim 1, further comprising:
    initializing a present sensor reading, previous sensor reading and a most-recent stable sensor reading to each be equal to a default sensor state, prior to said retrieving;
    setting a stable reading counter and reading change counter at a predetermined value, prior to said retrieving.

7. A method comprising:
    retrieving a present sensor reading;
    determining if the present sensor reading equals an immediately previous sensor reading;
    incrementing a reading change counter and setting a stable reading counter to a predetermined value in response to the present sensor reading not equaling an immediately previous sensor reading;
    determining if a change in the reading change counter is greater than or equal to a reading change tolerance;
    reporting a sensor reading bouncing error and resetting the reading change counter to a predetermined value in response to the reading change counter being greater than or equal to a reading change tolerance;
    incrementing said stable reading counter in response to the present sensor reading equaling the immediately previous sensor reading;
    determining if a change in said stable reading counter is greater than or equal to a stable reading tolerance;
    resetting said stable reading counter and reading change counter to a predetermined value in response to said stable reading counter being greater than or equal to a stable reading tolerance;
    determining if said present sensor reading is not equal to said most-recent stable sensor reading;
    reporting a state change event and setting said most-recent stable sensor reading equal to said present sensor reading in response to said present sensor reading not being equal to said most-recent stable sensor reading; and
    setting said previous sensor reading to said present sensor reading.

8. The method of claim 7 further comprising repeating said retrieving, determinings, incrementings, reportings, resetting and setting.

9. The method of claim 7 further comprising repeating said retrieving, determinings, incrementings, reportings, resetting and setting in response to the reading change counter being less than a reading change tolerance.

10. The method of claim 7 further comprising repeating said retrieving, determinings, incrementings, reportings, resetting and setting in response to said stable reading counter being less than a stable reading tolerance.

11. The method of claim 7 further comprising repeating said retrieving, determinings, incrementings, reportings, resetting and setting in response to said present sensor reading being equal to said most-recent stable sensor reading.

12. The method of claim 7, further comprising:
initializing a present sensor reading, previous sensor reading and a most-recent stable sensor reading to each be equal to a default sensor state, prior to said retrieving;
setting a stable reading counter and reading change counter at a predetermined value, prior to said retrieving.

13. A computer program product comprising:
a computer usable medium having computer readable program code means embodied therein for causing a computer to, in iterative fashion:
retrieve a sensor reading;
determine if said sensor reading represents a changed sensor reading;
increment a reading change counter and set a stable reading counter to a predetermined value in response to the sensor reading having changed;
determine if a changed sensor reading is indicative of toggling;
report a sensor reading bouncing error and reset the reading change counter to a predetermined value in response to the reading change indicating the sensor reading is toggling;
increment said stable reading counter in response to the sensor reading having not changed;
determine if the unchanged sensor reading is stable;
reset said stable reading counter and said reading change counter to a predetermined value in response then unchanged sensor reading being stable;
determine if a stable unchanged sensor reading is different from a most-recent stable sensor reading;
report a state change event and set said most-recent stable sensor reading to be equal to the stable unchanged sensor reading; and
set a previous sensor reading to be equal to said sensor reading.

14. The computer program product of claim 13 wherein said code means further comprises code means for causing a computer to:
initialize a present sensor reading to be equal to a default sensor state value;
initialize said previous sensor reading to be equal to a default sensor state value;
initialize said most-recent stable sensor reading to be equal to a default sensor state value;
initialize said stable reading counter at a predetermined value; and
initialize said reading change counter at a predetermined value.

15. The computer program product of claim 13 wherein said code means loops in response to first said sensor reading not toggling.

16. The computer program product of claim 13 wherein said code means loops in response to said sensor reading not being stable.

17. The computer program product of claim 13 wherein said code means loops in response to said sensor reading being the same as a most-recent stable sensor reading.

18. The computer program product of claim 13 wherein said code means determines if said sensor reading represents a changed sensor reading by determining if the retrieved sensor reading equals an immediately previous sensor reading.

19. The computer program product of claim 13 wherein said code means determines if a changed sensor reading is indicative of toggling by determining if a count of changes in the sensor state value has achieved a threshold.

20. The computer program product of claim 13 wherein said code means determines if the unchanged sensor reading is stable by determining if a count of stable sensor readings is greater than or equal to a stable reading sensor tolerance.

21. A system comprising:
means for retrieving a present sensor reading;
means for determining if the present sensor reading equals an immediately previous sensor reading;
means for incrementing a reading change counter and setting a stable reading counter to a predetermined value in response to the present sensor reading not equaling an immediately previous sensor reading;
means for determining if a change in the reading change counter is greater than or equal to a reading change tolerance;
means for reporting a sensor reading bouncing error and resetting the reading change counter to a predetermined value in response to the reading change counter being greater than or equal to a reading change tolerance;
means for incrementing said stable reading counter in response to the present sensor reading equaling the immediately previous sensor reading;
means for determining if a change in said stable reading counter is greater than or equal to a stable reading tolerance;
means for resetting said stable reading counter and reading change counter to a predetermined value in response to said stable reading counter being greater than or equal to a stable reading tolerance;
means for determining if said present sensor reading is not equal to said most-recent stable sensor reading;
means for reporting a state change event and setting said most-recent stable sensor reading equal to said present sensor reading in response to said present sensor reading not being equal to said most-recent stable sensor reading; and
means for setting said previous sensor reading to said present sensor reading.

* * * * *